(12) United States Patent
Zamd et al.

(10) Patent No.: US 11,666,692 B2
(45) Date of Patent: Jun. 6, 2023

(54) PORTABLE ULTRAFILTRATION DEVICE

(71) Applicant: HASSAN II UNIVERSITY OF CASABLANCA, Casablanca (MA)

(72) Inventors: Mohamed Zamd, Casablanca (MA); Benyounes Ramdani, Casablanca (MA); Abdellah Ait Taleb, Casablanca (MA); Abdellah Boualam, Casablanca (MA)

(73) Assignee: HASSAN II UNIVERSITY OF CASABLANCA, Casablanca (MA)

( * ) Notice: Subject to any disclaimer, the term of this patent is extended or adjusted under 35 U.S.C. 154(b) by 619 days.

(21) Appl. No.: 16/347,606

(22) PCT Filed: Nov. 3, 2017

(86) PCT No.: PCT/MA2017/000022
§ 371 (c)(1),
(2) Date: Jul. 18, 2019

(87) PCT Pub. No.: WO2018/084690
PCT Pub. Date: May 11, 2018

(65) Prior Publication Data
US 2019/0328951 A1 Oct. 31, 2019

(30) Foreign Application Priority Data
Nov. 7, 2016 (MA) .......................... 39440

(51) Int. Cl.
*A61M 1/34* (2006.01)

(52) U.S. Cl.
CPC ..... *A61M 1/341* (2014.02); *A61M 2205/3331* (2013.01); *A61M 2205/50* (2013.01);
(Continued)

(58) Field of Classification Search
CPC ...... A61M 1/16; A61M 1/341; A61M 1/3639; A61M 2205/3331; A61M 2205/50;
(Continued)

(56) References Cited

U.S. PATENT DOCUMENTS

| 4,269,708 A | 5/1981 | Bonomini et al. |
| 7,645,253 B2 | 1/2010 | Gura et al. |

(Continued)

FOREIGN PATENT DOCUMENTS

| CN | 2424776 Y | 3/2001 |
| CN | 101208119 A | 6/2008 |

(Continued)

OTHER PUBLICATIONS

International Search Report and Written Opinion dated Mar. 27, 2018 for corresponding International Application No. PCT/MA2017/000022, filed Nov. 3, 2017 (11 pages) with WIPO machine English translation (6 pages).

(Continued)

*Primary Examiner* — Patrick Orme
(74) *Attorney, Agent, or Firm* — Daniel F. Nesbitt; Nesbitt IP LLC

(57) ABSTRACT

A portable ultrafiltration device having a suction bellows connected to a tube, passing through a solenoid valve, to a first dialysate connector of a hemofilter incorporated into a blood circuit having arterial lines, extending from a vascular access and passing through a peristaltic pump, and venous lines passing through an electronic safety block to the vascular access, and a second dialysate connector connected to an ultrafiltration pressure sensor. The elements of the portable ultrafiltration device are connected and controlled by an intelligent central unit powered by a rechargeable battery. Liquid collects in the space surrounding the fibres and in the suction bellows until the space is completely full.

19 Claims, 1 Drawing Sheet

(52) U.S. Cl.
CPC . *A61M 2205/581* (2013.01); *A61M 2205/583* (2013.01); *A61M 2205/8206* (2013.01); *A61M 2209/088* (2013.01)

(58) Field of Classification Search
CPC ...... A61M 2205/581; A61M 2205/583; A61M 2205/584; A61M 2205/8206; A61M 11/1601; A61M 11/34; A61M 11/341
See application file for complete search history.

(56) References Cited

U.S. PATENT DOCUMENTS

| | | | |
|---|---|---|---|
| 8,211,047 B2 | 7/2012 | Cerasoli et al. | |
| 9,623,164 B2 | 4/2017 | Meyer et al. | |
| 2002/0187069 A1* | 12/2002 | Levin | A61M 1/34 422/44 |
| 2004/0254514 A1 | 12/2004 | Gura | |
| 2006/0009727 A1* | 1/2006 | O'Mahony | A61B 5/412 604/4.01 |
| 2006/0122552 A1* | 6/2006 | O'Mahony | A61M 1/34 604/6.11 |
| 2006/0157408 A1 | 7/2006 | Kuroda et al. | |
| 2007/0235376 A1 | 10/2007 | Daniel | |
| 2009/0093747 A1* | 4/2009 | Cerasoli | A61M 1/3621 604/6.09 |
| 2011/0105982 A1 | 5/2011 | Leonard et al. | |
| 2014/0091018 A1 | 4/2014 | Nilsson | |
| 2014/0231350 A1 | 8/2014 | Levin et al. | |

FOREIGN PATENT DOCUMENTS

| | | |
|---|---|---|
| CN | 105025951 A | 11/2015 |
| EP | 1 666 078 | 6/2006 |
| EP | 2219703 B1 | 3/2013 |
| JP | 2004-248844 A | 9/2004 |
| JP | 2007-502682 A | 2/2007 |
| JP | 2008-540018 A | 11/2008 |
| JP | 2011-514182 A | 5/2011 |
| WO | 9529731 | 11/1995 |
| WO | 2006123308 A2 | 11/2006 |
| WO | 2016072826 | 5/2016 |

OTHER PUBLICATIONS

First Office Action dated Jan. 19, 2021 in related Japanese Application No. 2019-545229 filed Apr. 26, 2019 (3 pages) with translation (3 pages).
First Office Action dated Apr. 2, 2021 in related Chinese Application No. 201780078156.3 filed Jun. 17, 2019 with Search Report (9 pages) with CNIPA machine translation (10 pages).
First Office Action dated Oct. 19, 2021 in related Indian Application No. 201927022609 filed Jun. 7, 2019 (5 pages).
Office Action dated Oct. 21, 2021 in related ARIPO Application No. AP/P/2019/011622 filed May 29, 2019 (5 pages).
Second Office Action dated Dec. 14, 2021 in related Chinese Application No. 201780078156.3 filed Jun. 17, 2019 (6 pages) with CNIPA machine translation (9 pages).

* cited by examiner

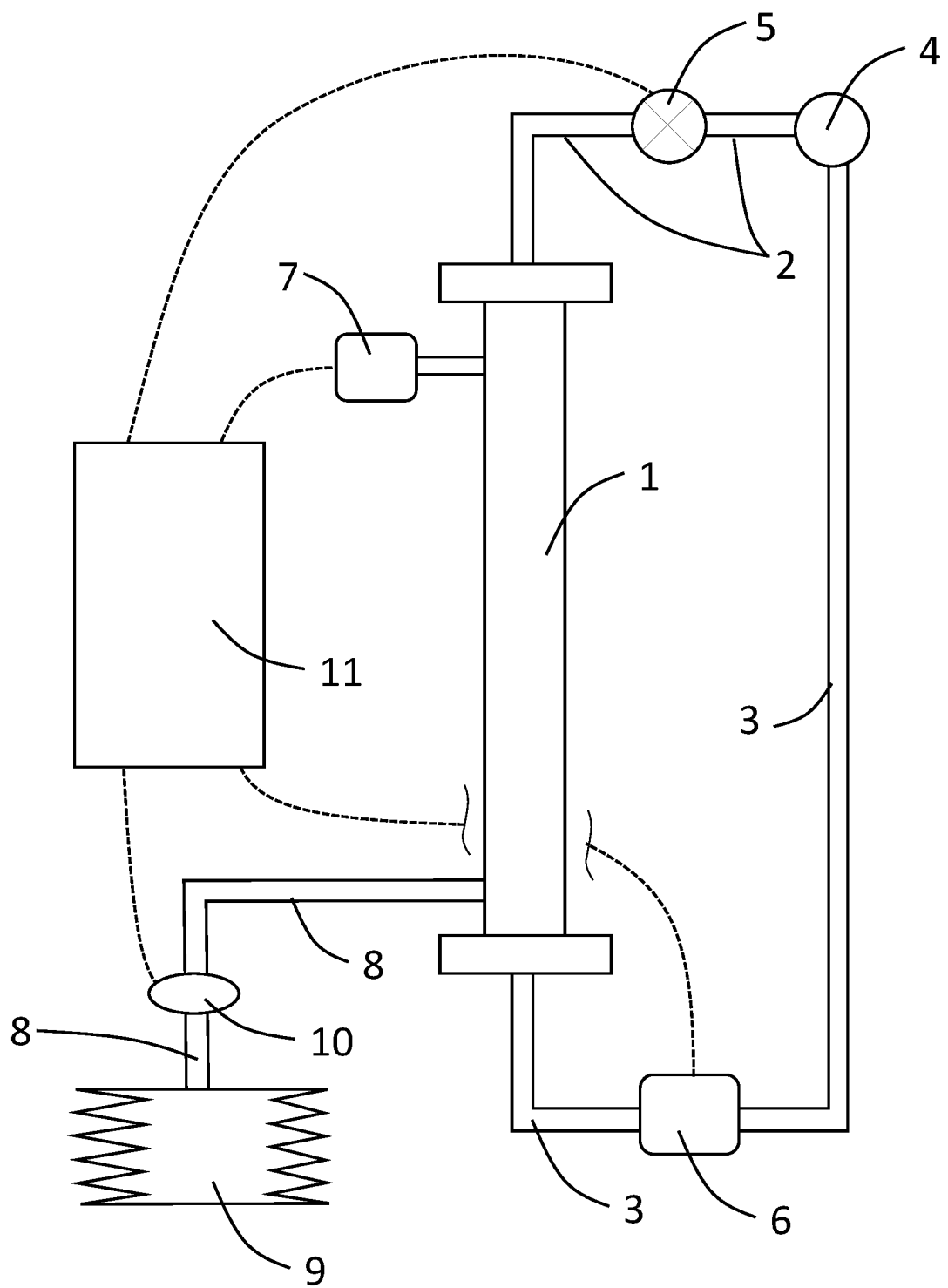

PORTABLE ULTRAFILTRATION DEVICE

BACKGROUND OF INVENTION

The present invention relates to a portable ultrafiltration device.

The excess of liquid within the extracellular compartment is a common situation in the medical field. Various types of patients are affected and it conditions the vital prognosis for short and long terms. The patients concerned by this situation are those having a (chronic or acute) kidney failure and/or a heart failure. Upon occurrence of the latter, especially for late stages, a kidney failure is often associated, making the use of diuretics (drugs intended to remove the excess of liquid through the kidney) hardly efficient, even entirely inefficient. In all these situations, resorting to a liquid extraction directly from the blood becomes necessary and urgent.

Currently, this extraction, also called ultrafiltration, is performed by means of large machines in a hospital environment and requires the immobilization of the patient during the entire intervention (which can last up to 4 hours). Several attempts for miniaturizing the ultrafiltration machines have been made, without achieving a device secure and efficient enough to be used on human beings on a large scale.

We have published a first patent in this field on 12 May 2016 under no WO2016/072826. The trials performed on prototype for the validation thereof objectified a very high ultrafiltration efficiency (extraction of one third of the volume of a blood bag in less than thirty minutes). Furthermore, due to its design, it was impossible for us to control of the extracted volume: once the process is initiated, the ultrafiltration continues until the plastic shell surrounding the hemofilter is filled. By extrapolation on a living system, such a quick loss of liquid without any control means would result in an irreversible state of shock.

SUMMARY OF INVENTION

The device according to the invention allows to solve this problem of safety while preserving the portable character and the simplicity of use of the device.

Indeed, according to a first feature, it comprises a blood circuit consisting of a hemofilter connected on either side to plastic tubes called arterial and venous lines. The arterial line connects the vascular access (an arterio-venous fistula or a double-lumen venous catheter) to the hemofilter and passes through a peristaltic pump having rollers intended to convey the blood into the blood circuit. The venous line follows the hemofilter and passes through an electronic safety block comprising a venous pressure sensor and an air sensor (allowing to challenge the risk of gas embolism) before reaching the vascular access. An ultrafiltration pressure sensor (which measures the pressure within the compartment surrounding the hollow fibers of the hemofilter) is mounted on one of the dialysate connectors of the hemofilter. A tube is mounted on the other connector and connects said connector to a suction bellows and passes through a solenoid valve. The peristaltic pump with rollers, the electronic safety block, the ultrafiltration pressure sensor and the solenoid valve are connected, controlled and managed by an intelligent central unit powered by a rechargeable battery.

The operation of the device is as follows: the patient's blood is collected from the vascular access and flows under the effect of the pump in the arterial line, then passes through the hemofilter to come back to the vascular access via the venous line. The negative pressure generated by the suction bellows is transmitted through the connection tube and causes the ultrafiltration of the blood through the fibers of the hemofilter. Thus, liquid builds up in the space surrounding the fibers until the outer shell of the hemofilter is entirely filled, then by the connection tube, builds up in the suction bellows until the latter is entirely filled. As the suction bellows fills up, the negative pressure that it exerts decreases up to becoming zero, then subsequently increases slowly until it reaches the level of the pressure in the blood contained in the fibers. At that moment, the ultrafiltration stops and the central unit indicates to the user that the treatment is finished by means of a visual or audible alarm. The blood is returned to the patient by means of the infusion of an isotonic physiological solution. The hemofilter and the suction bellows are then removed from the device. The intelligent central unit controls the start, the stop and the rotation speed of the blood pump, allows to detect air in the venous line and continuously records the pressures from the (venous and ultrafiltration) pressure sensors. These last two measurements, combined with the ultrafiltration coefficient of the hemofilter (inputted in the memory of the intelligent central unit at the beginning of each treatment) allow the intelligent central unit to calculate in real time the extracted amount of liquid and to detect the end of the treatment when the venous and ultrafiltration pressures become equal. In case of intolerance or arterial pressure drop, it is possible at any time to stop the ultrafiltration process by means of a control on the intelligent central unit which operates the solenoid valve mounted on the tube connecting the dialysate connector of the hemofilter and the suction bellows. Thus, the transmission of the negative pressure is interrupted and the ultrafiltration immediately stops. The volume of the extracted liquid is that of the suction bellows being used (variable according to the patient's needs) and it is possible, if an additional volume is required, to change the suction bellows at the end of the treatment by simply operating the solenoid valve, removing the full suction bellows and installing a new empty bellows under vacuum.

BRIEF DESCRIPTION OF DRAWING

The appended drawing illustrates the invention:

FIG. 1 shows a diagram of the device according to the invention.

DETAILED DESCRIPTION OF INVENTION

In reference to this drawing, the device consists of a blood circuit constituted by a hemofilter (1) connected on either side to plastic tubes called arterial (2) and venous (3) lines. The arterial line (2) connects the vascular access (4) (an arterio-venous fistula or a double-lumen venous catheter) to the hemofilter (1) and passes through a peristaltic pump (5) having rollers intended to convey the blood into the blood circuit. The venous line (3) follows the hemofilter (1) and passes through an electronic safety block (6) comprising a venous pressure sensor and an air sensor before reaching the vascular access (4). An ultrafiltration pressure sensor (7) (which measures the pressure within the compartment surrounding the hollow fibers of the hemofilter) is mounted on one of the dialysate connectors of the hemofilter. A tube (8) is mounted on the other connector and connects said connector to a suction bellows (9) and passes through a solenoid valve (10). The peristaltic pump having rollers (5), the electronic safety block (6), the ultrafiltration pressure sensor (7) and the solenoid valve (10) are connected and controlled by an intelligent central unit (11) powered by a rechargeable battery.

The patient's blood is collected from the vascular access (4) and flows under the effect of the pump (5) in the arterial line (2), and passes through the hemofilter (1) to come back to the vascular access (4) via the venous line (3). An injection of anticoagulation is required to maintain the fluidity of the blood in the blood circuit. The negative pressure generated by the suction bellows (9) is transmitted through the connection tube (8) and causes the ultrafiltration of the blood through the fibers of the hemofilter (1). Thus, liquid builds up in the space surrounding the fibers up to the outer shell of the hemofilter (1) is entirely filled, then by the connection tube (8), builds up in the suction bellows (9) until the latter is entirely filled. As the suction bellows (9) fills up, the negative pressure that it exerts decreases to zero and subsequently increases slowly until it reaches the level of the pressure in the blood contained in the fibers. At that time, the ultrafiltration stops and the central unit (11) indicates to the user the end of the treatment by means of a visual or audible alarm. The blood is returned to the patient by means of the infusion of an isotonic physiological solution. The hemofilter (1) and the suction bellows (9) are then removed from the device. The intelligent central unit (11) controls the start, the stop and the rotation speed of the blood pump (5), allows to detect air in the venous line (3) and continuously records the pressures from the venous pressure sensors from the electronic safety block (6) and the ultrafiltration pressure from the sensor (7) located on the dialysate connector of the hemofilter (1). These last two measurements, combined with the ultrafiltration coefficient of the hemofilter (1) (inputted in the memory of the intelligent central unit (11) at the beginning of each treatment) allow the intelligent central unit (11) to calculate in real time the extracted amount of liquid and to detect the end of the treatment when the venous and ultrafiltration pressures become equal. In case of intolerance or arterial pressure drop, it is possible at any time to stop the ultrafiltration process by means of a control on the intelligent central unit (11) which operates the solenoid valve (10) mounted on the tube (8) connecting the dialysate connector of the hemofilter (1) and the suction bellows (9). Thus, the transmission of the negative pressure is interrupted and the ultrafiltration immediately stops. The volume of the extracted liquid is that of the suction bellows (9) being used (variable according to the patient's needs) and it is possible, if an additional volume is required, to change the suction bellows (9) at the end of the treatment by simply operating the solenoid valve (10), removing the full suction bellows (9) and installing a new empty bellows under vacuum.

The present invention is in no way limited to the embodiments as described and shown, but the one skilled in the art will know how to provide any variation in accordance with the spirit thereof.

The expected advantages of the present invention are numerous. Its ease of manufacture and the modest cost of its components allow to make it a low-cost tool in order to treat a disease which is extremely common and often has an unfortunate prognosis. The current costs of the water salt overload threaten the health budgets of several states. It could constitute a real alternative in lower-income areas, especially for the treatment of acute kidney failure complicated with water salt overload. The portability of the apparatus allows to release the patients with heart and/or kidney failure from the ultrafiltration machines and from the iterative hospitalizations which often result from overload accidents. Thus, it could allow a better socio-professional insertion. The variability of the intensity of the liquid extraction allows to reduce the impact on the heart: the extraction is maximal at the beginning when the blood volume is high, and exponentially decreases as the suction bellows fills up and the absolute value of the negative pressure decreases. Furthermore, the volume of the suction bellows being defined in advance, no overachievement is possible. A daily and regular use of this device could improve the often unfortunate cardiovascular prognosis of the patients suffering from water salt overload. The ecological dimension of this method cannot be denied as it allows very important savings in water, electricity and waste production with high infectious risk.

The invention claimed is:

1. A portable ultrafiltration device, comprising
   a. a blood circuit consisting of (i) an arterial line extending from a vascular access blood circuit would consist of electronic safety block and passing through a peristaltic pump, and (ii) a venous line passing through an electronic safety block and connecting to the vascular access;
   b. a hemofilter incorporated into the blood circuit between the arterial line and the venous line, the hemofilter including a first dialysate connector and a second dialysate connector;
   c. a suction bellows connected to a tube passing through a solenoid valve to the first dialysate connector of the hemofilter; and
   d. an ultrafiltration pressure sensor connected to the second dialysate connector of the hemofilter,
   wherein the solenoid valve can interrupt the transmission of a negative pressure exerted by the suction bellows, and immediately stop the ultrafiltration.

2. The portable ultrafiltration device according to claim 1, wherein the peristaltic pump, the electronic safety block, the ultrafiltration pressure sensor and the solenoid valve are connected and controlled by an intelligent central unit powered by a rechargeable battery.

3. The portable ultrafiltration device according to claim 2, wherein the intelligent central unit operates the solenoid valve to stop an ultrafiltration procedure at any time and at a user request.

4. The portable ultrafiltration device according to claim 3, wherein the intelligent central unit indicates to a user of a time of an end of a treatment, with a visual or audible alarm.

5. The portable ultrafiltration device according to claim 2, wherein the intelligent central unit indicates to a user a time of an end of a treatment, with a visual or audible alarm.

6. The portable ultrafiltration device according to claim 2, wherein the electronic safety block consists of a venous pressure sensor which transmits in real time the level of the pressure in hollow fibers of the hemofilter to the intelligent central unit, and of an air sensor on the venous line.

7. The portable ultrafiltration device according to claim 1, wherein the electronic safety block consists of a venous pressure sensor which transmits in real time a level of the pressure in hollow fibers of the hemofilter to an intelligent central unit, and of an air sensor on the venous lines.

8. The portable ultrafiltration device according to claim 7, wherein the intelligent central unit calculates in real time an extracted amount of liquid on the basis of data transmitted by the venous pressure sensor of the electronic safety block and by the ultrafiltration pressure sensor.

9. The portable ultrafiltration device according to claim 8, wherein the intelligent central unit operates the solenoid valve to stop an ultrafiltration procedure at any time and at a user request.

10. The portable ultrafiltration device according to claim 8, wherein the intelligent central unit indicates to a user of a time of an end of a treatment, with a visual or audible alarm.

11. The portable ultrafiltration device according to claim 7, wherein the intelligent central unit operates the solenoid valve to stop an ultrafiltration procedure at any time and at a user request.

12. The portable ultrafiltration device according to claim 7, wherein the intelligent central unit indicates to a user of a time of an end of a treatment, with a visual or audible alarm.

13. The portable ultrafiltration device according to claim 1, wherein the bellows of the dialysate liquid circuit applies a negative pressure to the hemofilter, and the filling of the bellows provides an exponential decrease in the extraction of the dialysate liquid.

14. A portable ultrafiltration device, consisting of:
(i) a hemofilter comprising an arterial connection and a venous connection, a first dialysate connector, a second dialysate connector, a compartment in liquid communication with the first dialysate connector and the second dialysate connector, and hollow fibers in liquid communication between the arterial connection and the venous connection, surrounded by the compartment;
(ii) an arterial line extending from a vascular access to the arterial connection of the hemofilter,
(iii) a peristaltic pump that is electronically controlled and through which passes the arterial line;
(iv) a venous line extending from the venous connection of the hemofilter to the vascular access;
(v) a safety block that is electronically controlled and through which passes the venous line, the safety block consisting of a venous pressure sensor and an air sensor on the venous line;
(vi) a suction bellows connected to the first dialysate connector by a dialysate tube;
(vii) an optional solenoid valve through which the dialysate tube passes;
(viii) an ultrafiltration pressure sensor connected to the second dialysate connector; and
(ix) an intelligent central unit powered by a rechargeable battery that is electronically connected to and/or controls the peristaltic pump, the electronic safety block, the ultrafiltration pressure sensor, and the optional solenoid valve.

15. The portable ultrafiltration device according to claim 14, wherein the ultrafiltration pressure sensor transmits in real time a level of the pressure in the hollow fibers of the hemofilter to the intelligent central unit.

16. The portable ultrafiltration device according to claim 15, wherein the intelligent central unit calculates in real time an extracted amount of liquid on the basis of data transmitted by the venous pressure sensor of the electronic safety block and by the ultrafiltration pressure sensor.

17. The portable ultrafiltration device according to claim 16, which includes the solenoid valve, wherein the intelligent central unit operates the solenoid valve to stop an ultrafiltration procedure at any time and at a user request.

18. The portable ultrafiltration device according to claim 14, wherein the intelligent central unit indicates to a user a time of an end of a treatment, with a visual or audible alarm.

19. The portable ultrafiltration device according to claim 14, wherein the suction bellows applies a negative pressure to the hemofilter, and the filling of the bellows provides an exponential decrease in the extraction of the dialysate liquid.

* * * * *